United States Patent [19]

Chen et al.

[11] 4,099,530
[45] Jul. 11, 1978

[54] CARDIAC PACER CIRCUITRY TO FACILITATE TESTING OF PATIENT HEART ACTIVITY AND PACER PULSES

[75] Inventors: Chieh Y. Chen, Billerica; Wesley R. Grace, Andover, both of Mass.

[73] Assignee: American Pacemaker Corporation, Woburn, Mass.

[21] Appl. No.: 791,552

[22] Filed: Apr. 27, 1977

[51] Int. Cl.$^2$ .................................................. A61N 1/36
[52] U.S. Cl. ........................ 128/419 PT; 128/419 PG
[58] Field of Search .................... 128/419 PG, 419 PT

[56] References Cited

U.S. PATENT DOCUMENTS

| | | | |
|---|---|---|---|
| 3,718,909 | 2/1973 | Greatbatch | 128/419 PT |
| 3,756,245 | 9/1973 | Thaler et al. | 28/419 PT |
| 3,774,619 | 11/1973 | Goldberg | 128/419 PT |
| 4,041,954 | 8/1977 | Ohara | 128/419 PT |

Primary Examiner—William E. Kamm
Attorney, Agent, or Firm—Weingarten, Maxham & Schurgin

[57] ABSTRACT

A demand cardiac pacer having provisions for determining power source life status both during normal heart operation and during heart stimulation by the pacer. An external magnetic pulse of relatively long duration induces a test mode in the circuit, the pacer reverting to the pacing mode immediately after removal of the magnetic stimulus. When producing pacing pulses in the pacing mode, testing of the patient's heart is facilitated by providing an external magnetic pulse of relatively short duration which is insufficient to place the pacer in the test mode but of sufficient length to inhibit pacing pulses. This invention applies to preset frequency pacers as well as to programmable pacers and includes means for observing the preprogrammed pulse frequency immediately after programming.

13 Claims, 6 Drawing Figures

CARDIAC PACER CIRCUITRY TO FACILITATE TESTING OF PATIENT HEART ACTIVITY AND PACER PULSES

FIELD OF THE INVENTION

This invention relates generally to implantable heart stimulating devices and more particularly concerns a pacer circuit subject to external control to provide test mode pulses, pacing mode pulses and to provide inhibition of all pacer pulses.

DISCUSSION OF THE PRIOR ART

It has previously been known to induce a test mode in a pacer whereby stimulating pulses of a frequency differing from the pacing pulse frequency may be used to determine the remaining useful life of the implanted power source. U.S. Pat. No. 3,774,619 describes certain methods and apparatus for externally controlling the operation of implantable heart pacers for such test purposes. In particular, it describes circuitry for providing a test mode whereby the stimulating rate is dependent upon and indicative of remaining life of the power source. By knowing the characteristics of the pacer, power source life can be determined by measuring the frequency difference between the test mode pulses and the pacing mode pulses. This patent also describes a method, during normal heart beat activity, for inferring the demand or pacing rate by inducing an interference mode rate upon the pacer.

Additionally, it has been possible to determine remaining battery life without having access to the life characteristics of the pacer since it has been found that in present day pacers the difference between the test rate and the demand or pacing rate can be practically controlled so as to change little with minor variations in the production process and with component age. However, decreases in the remaining life of the power source will cause an easily noticeable and predictable change in the frequency difference. Since the difference between the test mode frequency and the demand mode frequency depends only on the remaining life of the power source and will be substantially the same for all pacers of a particular design, a reference chart showing preimplantation measurements of the pacer rate is not necessary. Furthermore, reasonable variations in the accuracy of the measuring equipment has substantially no effects upon such tests, since two frequencies are being measured and the frequency difference between them is the useful factor being determined.

As stated in the above-mentioned patent, the demand rate can be made substantially independent of the remaining power source life while the test rate is directly dependent upon the power source life and the measurable difference between them provides the desired information. However, there are drawbacks to the previously known testing methods mentioned above, one of them being that where the patient has a normal heart activity at the time of the implanted pacer evaluation, the pacing or demand rate is not immediately available. There are methods for inhibiting the patient's own heart action in order to test an implanted pacer but this is extremely undesirable and may be dangerous to the patient. The above-mentioned patent discloses a method by which a pulse rate similar to the demand rate can be induced in the pacer through external application of electrical interference. This method has the disadvantage of requiring additional constraints on the design and manufacture to ensure that the relationship between demand and interference rate is a constant, which may not be obtainable in any commercially feasible manner. Also, the method of this patent requires additional special equipment for the application of the interfering signal. Acquisition and maintenance of such equipment may not be desirable on the part of a doctor who is charged with evaluating the implanted pacer.

Programmable pacers have been made in which the pacing rate of the implanted pacer can be changed. In the presence of normal heart activity on the part of the patient, there has not been available any convenient means to check whether the pacer has been properly programmed immediately after the programming has been accomplished, which also allows means for checking the power source status without reference to prior pacer history.

SUMMARY OF THE INVENTION

It is an object of this invention to be able to measure both the demand and test rates of a pacer, whether or not the patient has normal heart action, in order to determine power source life status. Furthermore, this invention permits these rates to be satisfactorily determined using equipment customarily available in a doctor's office.

It is another object of the invention to be able to stop pacing pulses when desired so that the patient's own heart activity can be observed and a normal electrocardiogram made.

Broadly speaking, the invention comprises externally controlled implanted test mode circuitry arranged to produce a heart stimulation rate in addition to the demand rate, where one rate is preferably dependent upon the remaining useful life of the power source and the other rate is substantially independent of the remaining useful life of the power source. Both rates could be dependent upon power source useful life as long as the rates are different; it is the rate difference which is directly indicative of that remaining life. The circuit includes a magnetically operated reed switch and other circuit components to cause different pacer stimulation rates in the test and demand modes of operation. The difference between test and demand rates are controlled such that a first predetermined range of difference indicates satisfactory remaining life in the power source, and a second predetermined range of difference above a predetermined minimum threshold level indicates insufficient remaining power source life requiring early replacement of the pacer.

The test rate is produced by application of a magnetic field external to the patient's body. The magnetic field must be applied as long as the test rate is desired to be produced. The demand rate is produced upon removal of the magnet from the vicinity of the patient and delay circuitry allows a few seconds of demand rate pulses. The circuitry includes provision for storing energy during the application of the magnet, which energy is released in a controlled manner following removal of the magnet such that the heart beat sensing circuitry of the pacer is prevented from detecting heart beats for a predetermined period of time. Thus even when the patient has normal heart activity the demand rate can be simply induced and directly measured by observing the demand rate for a short period of time following removal of the magnet after inducing the test mode. The circuitry further includes provision for inhibiting demand mode pulses pursuant to short duration external magnetic pulses applied in the vicinity of the patient. This permits the patient's own heart activity to be evaluated without any interfering signals and in particular it permits the taking of a normal electrocardiogram for diagnostic purposes.

BRIEF DESCRIPTION OF THE DRAWING

The objects, advantages and features of this invention will be more readily apparent from the following detailed description when taken in conjunction with the accompanying drawing in which.

DESCRIPTION OF THE PREFERRED EMBODIMENTS

Figure 1:
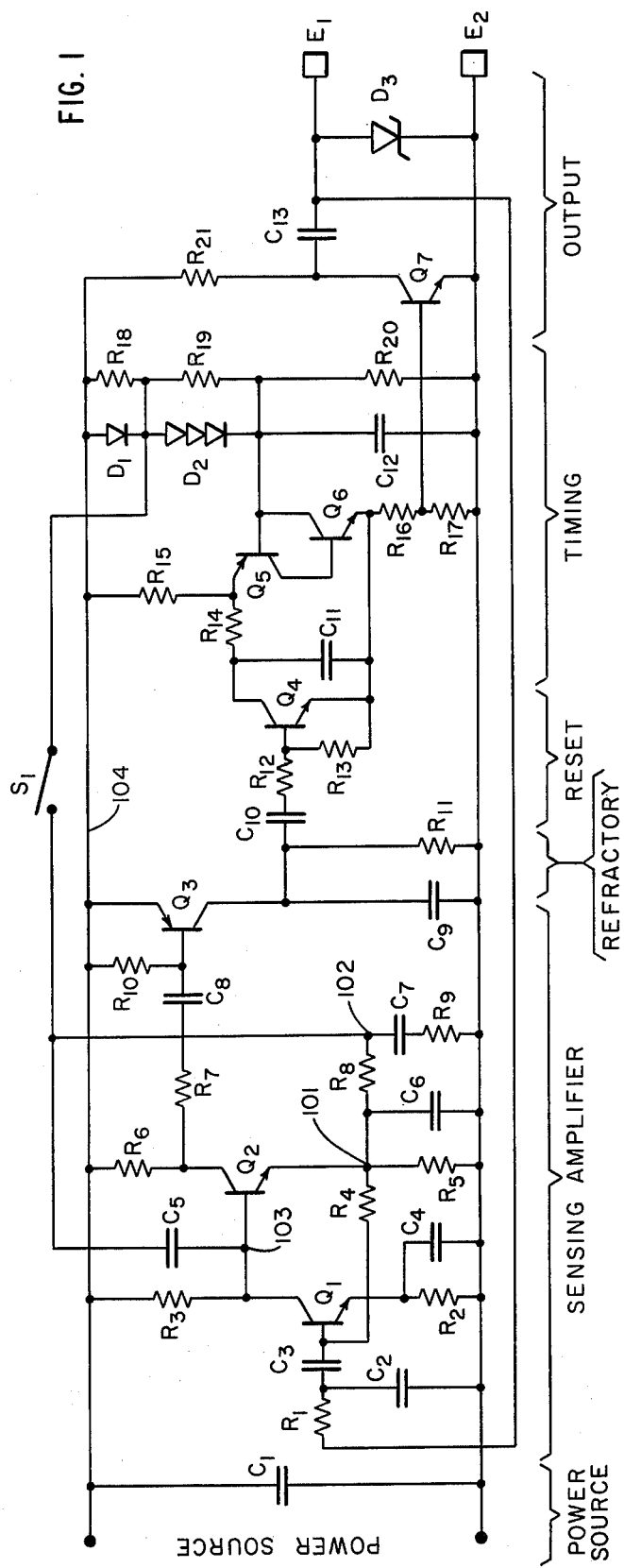
FIG. 1 is a schematic diagram of the pacer circuit of the present invention.

In view of the well-known operation of demand cardiac pacers, the basic operation of FIG. 1 will not be discussed in detail herein. Operative portions of the circuit are indicated by labeled brackets located below the circuit diagram itself. Reference is hereby made to U.S. Pat. No. 3,345,990 disclosing a demand pacer which provides electrical stimulating impulses to the patient's heart only in the absence of natural heart beats. U.S. Pat. No. 3,528,428 is an improvement upon the earlier demand pacer and provides a circuit which is not susceptible to stray signals which could erroneously cut off the generation of heart-stimulating impulses. Previously mentioned U.S. Pat. No. 3,774,619 discloses a means for testing the extent of use or the remaining power available in the pacer power source in the circuit of U.S. Pat. No. 3,528,428.

This invention is an improvement over the latter patent and includes additional circuit components to enable an evaluator, normally a doctor, to test both the pacer and the patient independently of the pacing status of the pacer at any particular time. Capacitor C5 has been connected between magnetic reed switch S1 which is included within the implanted circuitry, and the base of transistor Q2 in the sensing amplifier of the pacer circuit. Capacitor C7 and resistors R8 and R9 have been added to the emitter circuit of transistor Q2 in the sensing amplifier. Otherwise, the circuit is substantially as disclosed in U.S. Pat. No. 3,774,619. These additional components operate in conjunction with the magnetic reed switch S1 and the sensing amplifier of the pacer circuit, in particular with resistor R5 and capacitor C6 of that amplifier, to affect the bias voltage at junction 101 and at the signal injection point 103 at the base of transistor Q2.

The operation of the circuit of FIG. 1 will now be discussed in detail in conjunction with timing diagrams shown in FIGS. 2-5. In its normal operation, the pacer circuit functions in the demand mode with switch S1 open. When the patient's heart is beating normally, the sensing amplifier of the pacer circuit inhibits the timing portion of the circuit from producing a pulse at the output. Each time the circuit senses a heart pulse, the reset portion of the circuit, which includes transistor Q4, operates to reset the timing portion of the circuit to produce a pulse at the output if the next heart beat does not occur at the appropriate time. In the absence of a beat of the patient's heart within a specified time determined by the timing portion of the circuit after the last heart beat or pacing pulse, the circuit will produce a pulse on the output terminals E1, E2.

During normal operation with S1 open, the bias voltage at junction 101 is normally quite low compared to the power source voltage. If the bias voltage at junction 101 is increased to approximately twice its normal value, a critical bias voltage (CB) is reached and the amplifier is prevented from sensing signals generated by the heart. To place the pacer into the test mode, switch S1 is closed by bringing a test magnet in the proximity of the pacer implanted in the patient. The magnet will preferably have a steady state magnetic field but may effectively have a relatively long duration pulse. Closure of switch S1 increases the bias voltage on junction 101 above the critical value thereby preventing sensing of heart beats. By thus inactivating the sensing amplifier, an evaluation of the pacer itself may be made as will be clearly indicated hereinbelow.

Figure 2:
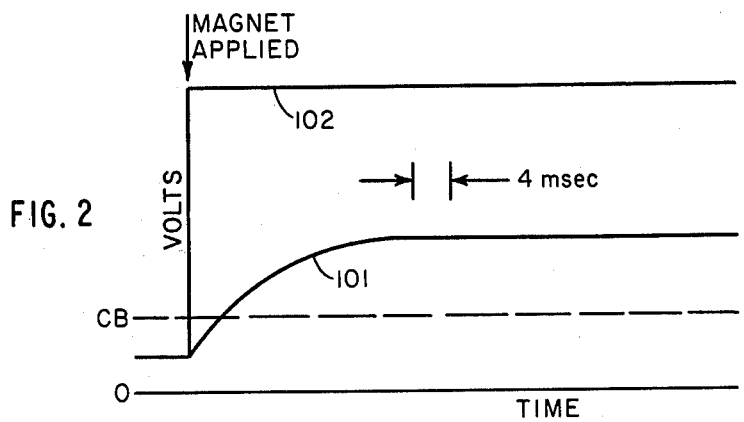
FIG. 2 is a timing diagram showing voltages when an external magnetic field of long duration is applied.

The addition of capacitor C7 and resistors R8 and R9 changes the time required for the voltage at junction 101 to vary in response to the closing or opening of switch S1. With reference to FIG. 2, it may be seen that when the magnet is applied at time T1, switch S1 closes, the voltage at junction 102 immediately rises to a value substantially similar to the power source voltage and the voltage at junction 101 rises to a value considerably higher than the critical or CB value in a time which is dependent upon the values of resistors R5, R8 and capacitor C6. This time may typically be approximately 20 milliseconds. During the closure of switch S1, capacitor C7 also charges to the same higher voltage level. The time required for charging capacitor C7 is longer than the time for the voltage at junction 101 to rise to that level and may typically be in the order of one second, depending upon the values of capacitor C7 and resistor R9.

Figure 3:
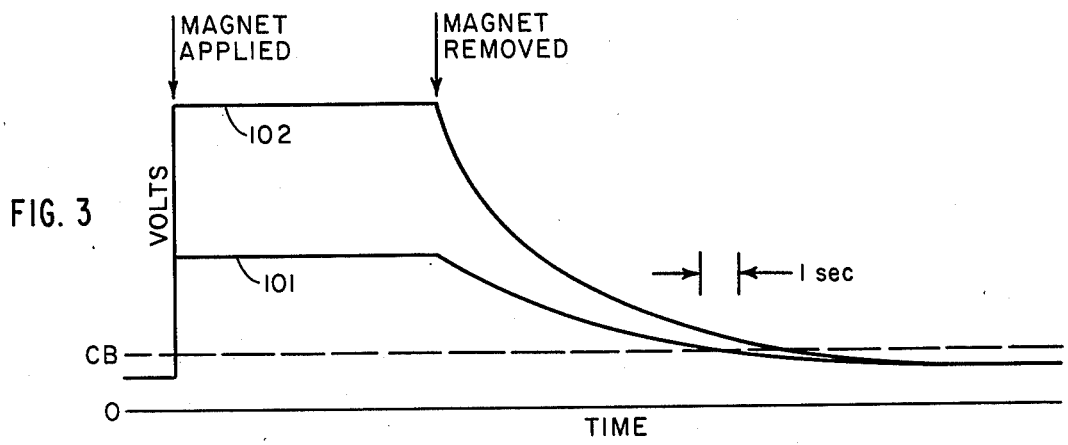
FIG. 3 is a timing diagram on a different scale showing voltages when the external magnetic field is removed.

Upon removal of the magnet, switch S1 opens and the voltage at junction 102 slowly decreases, depending upon the values of capacitor C7 and resistors R5, R8 and R9. This time for the reduction of the voltage on junction 102 may be in the order of 5-10 seconds. The voltage at junction 101 follows the voltage at junction 102 upon the opening of switch S1 but has approximately one-half the value of the voltage at 102, as indicated in FIG. 3, depending upon the values of the resistors R5, R8 and R9.

As stated previously, upon application of the magnet, switch S1 immediately closes and the bias voltage at junction 101 rises to the threshold level CB (FIG. 2) to inhibit operation of the sensing amplifier in a time (approximately 5 milliseconds) which is short compared to a heart or a pacer pulse-to-pulse interval. Thus the sensing function of the circuit is effectively inactivated immediately upon the application of the magnet. In accordance with U.S. Pat. No. 3,774,619, the pacer is then in the test mode and generates pulses at a rate different from the normal pacing rate. Either the test rate or the demand rate may be made frequency-dependent upon the remaining life of the batteries which provide the power in the implanted pacer. When the magnet is removed, switch S1 immediately opens and the voltage at junction 101 decreases slowly toward the CB level as shown in FIG. 3 so that the sensing amplifier continues to be inactivated for 5-10 seconds following removal of the magnet. Thus the pacer will not sense actual heart beats for that period of time and will operate to produce pacing pulses at its normal preset pacing rate which, as stated above, is different from the test rate induced during the application of the magnet.

It is important to note that a certain finite period of time is necessary to charge capacitor C7. Typically this capacitor will be fully charged after switch S1 has been closed for approximately one second but it is effective to produce a few pacing mode pulses with a lesser charge. The evaluator may then continue with the magnet applied in order to determine the test or magnet rate which normally takes several seconds, or he may immediately remove the magnet in order to induce the pacer to produce pulses at the preset pacer rate. If, for example, it takes 10 seconds to determine the magnet rate, capacitor C7 would long since have been fully charged and, upon removal of the magnet, the sensing amplifier would be inactivated for 5-10 seconds (a matter of choice depending upon component values). The pacer will operate at the preset pacer rate during the time interval in which capacitor C7 discharges to value CB.

While the previously mentioned U.S. Pat. No. 3,774,619 teaches how to induce a magnet or test rate, there was no disclosure of a capability to produce the demand or pacer rate if the heart is functioning normally. Because of this, it was found necessary, as disclosed in that patent, to induce an interference-continuous mode from which the demand mode rate could be inferred. As stated previously, application of the interference signal has several disadvantages and it is apparent from the above description that both the magnet or test mode rate and the demand or normal pacing rate may be measured directly by use of the present invention.

Figure 4:
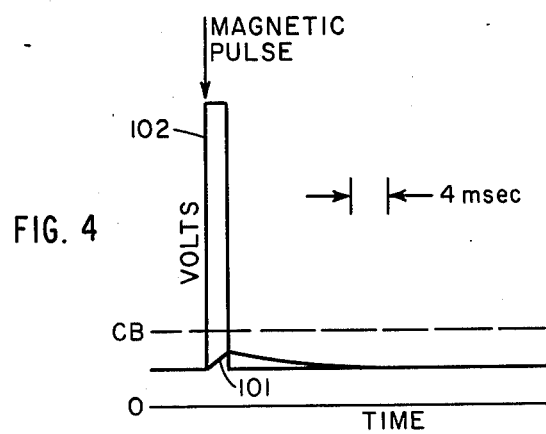
FIG. 4 is a timing diagram showing the results of applying a short duration magnetic pulse.

In accordance with this invention, when it is desired to evaluate the heart operation of a patient at a time when heart stimulation impulses are continuously required and the pacer is operating in its demand mode, a magnetic device such as an electromagnet may be brought into proximity with the implanted pacer and a short duration magnetic pulse applied to the pacer circuit as shown in FIG. 4. Such a pulse may be as short as one millisecond and as long as 50 milliseconds, but will preferably be in the range of 1-3 milliseconds. As indicated, the voltage at junction 102 rises immediately upon the short duration closure of switch S1 whereas the voltage at junction 101 rises only slightly due to the values of capacitor C6 and resistors R5 and R8. In such case the critical voltage CB is not reached during the application of one short pulse. Capacitor C7 and resistor R9 do not allow capacitor C7 voltage to reach a high enough value to bring the voltage at junction 101 above the critical value after application of the pulse. Capacitor C5 couples the pulse at junction 102 to signal injection point 103 at the base of transistor Q2. When a single pulse as indicated in FIG. 4 is applied to close switch S1 for a short time, the sensing amplifier is not inactivated. As noted previously, a predetermined period of time, for example 5 milliseconds, is required for the CB voltage level to be reached. In this manner each such short duration magnetic pulse actuates the sensing amplifier in such a way as to cause a reset of the pacer timing circuitry as though the magnetic pulse were a natural heart beat. One such pulse must be applied within each pulse-to-pulse interval to ensure no pacer impulses occur while the heart is being evaluated. In this manner, the pacing function is inhibited so that heart-stimulating impulses are not generated and any activity which exists in the patient's heart can be evaluated. Thus natural heart rhythms slower than the preset pacer rate can be observed and electrocardiograms can be taken which are undistorted by pacing pulses and are therefore suitable for diagnosis.

Figure 6:
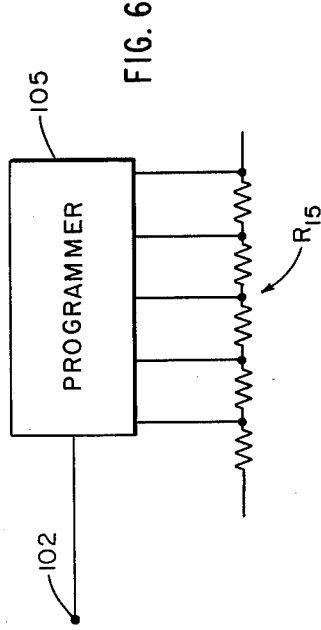
FIG. 6 is a partial schematic diagram indicating how FIG. 1 would be modified to make it a programmable pacer.
Figure 5:
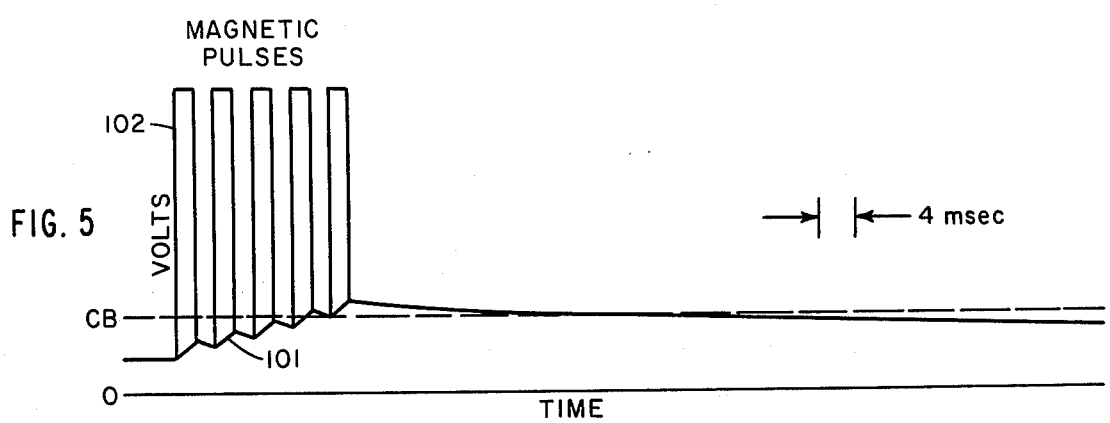
FIG. 5 is a timing diagram showing the voltages when several short duration magnetic pulses are applied.

It is possible to change the demand frequency of the timing circuitry portion of the pacer circuit of FIG. 1 by changing the circuit effective value of resistor R15. This can be done by means of a programming circuit 105 (as shown in FIG. 6) responsive to closing and opening of switch S1 as may be actuated by a series of magnetic pulses of the type shown in FIG. 5. The programmer 105 typically comprises a number of bilateral switches which can be actuated to short one or more of the segments of resistor R15. These switches may be operative in response to a particular coded series of short duration magnetic pulses as shown, and in the manner described in U.S. Pat. No. 3,805,796. Segmented resistor R15 shown in FIG. 6 would be connected in the circuit of FIG. 1 directly in place of the single element resistor R15 shown. The programmer 105 is connected between junction 102 and resistor R15. Because the charge time and discharge time for capacitor C7 are different, multiple short duration magnetic pulses have a cumulative effect on the circuit of this invention if they are closely spaced as shown in FIG. 5. By carefully choosing the component values of the circuit, it is possible to have a single short duration magnet pulse affect the circuit as described above, that is, inhibit pacing, while a train of several short duration magnetic pulses such as may be employed in programming an implanted pacer from outside the body, would raise the voltage at junction 101 above the critical CB level and thereby inactivate the sensing amplifier for several seconds following programming. Thus a closely spaced series of short pulses has the amplifier inactivating effect of a continuous or long duration pulse, but pacing pulses are not induced at the test mode rate. With this circuit one can determine immediately after programming whether or not the pacer has been properly programmed as intended. The amplifier is thus inactivated for several seconds following programming and the pacer then operates at the demand rate during that period of time, even though the heart may be beating normally. Proper programming may therefore be verified immediately following programming even in the presence of normal heart activity, in the same pacer having the ability to test power source life status.

Reference to programming herein has been only to changes of demand mode frequency. However, other parameters of the pacer can be changed by a series of magnetic pulses and it would be useful to be able to observe the demand rate immediately thereafter to check on proper operation after the changes have been made.

The components of the pacer circuit can have a range of values. For purposes of example only, the present invention will operate within the parameters described herein with capacitor C5 having a value in the range of 0.001 µf, capacitor C6 having a value in the range of 0.15 µf, resistors R5 and R8 having a resistance in the range of 330K ohms and resistor R9 having a value ranging between 20K and 150K ohms.

While switch S1 has been shown and described as a magnetic reed switch, it can be made responsive to other forms of energy such as electromagnetic (radio frequency, light) or acoustic. Furthermore, such a switch can be connected directly between junction 102 and power supply line 104. With this connection, a short duration energy pulse would be detected by the sensing amplifier and inhibit the pacer, and multiple short duration energy pulses which could be used for programming the pacer would inactivate the amplifier for a period of time following programming. As thus connected, this switch would not affect pacing rate.

It is likely that modifications and improvements will occur to those skilled in the pacer art which are within the scope of this invention.

What is claimed is:

1. An improved implantable electronic heart pacer having a self-contained power source, said pacer including terminal means for connection to the heart of a patient, pulse generator means connected to said terminal means for supplying stimulating pulses thereto, timing means for controlling the rate of delivery of said stimulating pulses, and heart beat detecting means for preventing delivery of said stimulating pulses when the patient has normal heart activity, said timing means having a test mode rate and a demand mode rate which is different from said test mode rate, at least one of said test mode rate and said demand mode rate being dependent upon remaining useful life of said power source, said improvement comprising:
    means responsive to an externally applied magnetic field, for inducing said timing means to operate at said test mode rate;
    delay means responsive to removal of said magnetic field for inducing said timing means to operate at said demand mode rate for a first predetermined period of time;
    means for inactivating said heart beat detecting means only after application of said magnetic field for a second predetermined period of time, said inactivating means being operative during application of said magnetic field and during said first predetermined period of said delay means;
    means responsive to an externally applied magnetic pulse having a duration which is short compared with the normal demand mode pulse-to-pulse interval to inhibit said pulse generator means when said pulse generator means is pacing in said demand mode.

2. The improved pacer recited in claim 1 wherein said second predetermined period of time is short compared with the normal demand rate pulse-to-pulse interval and long compared with the duration of said short duration magnetic inhibiting pulse.

3. The improved pacer recited in claim 2 wherein said magnetic inhibiting pulse has a duration in the range of 1-50 milliseconds.

4. The improved pacer recited in claim 1 and further comprising:
    means in said implantable electronic heart pacer for changing said demand mode rate in response to the application of a coded sequence of short duration closely spaced external magnetic pulses, said sequence of pulses being equivalent to application of said magnetic field for said second predetermined period of time;
    whereby said delay means is operative to induce said timing means to operate at said reprogrammed demand mode rate for said first predetermined period of time while said heart beat detecting means is inactivated.

5. An improved implantable electronic heart pacer having a selfcontained power source, said pacer including terminal means for connection to the heart of a patient, pulse generator means connected to said terminal means for supplying stimulating pulses thereto, timing means for controlling the rate of delivery of said stimulating pulses and having a demand mode rate, heart beat detecting means for preventing delivery of said stimulating pulses when the patient has normal heart activity, and means for resetting said timing means upon detection of each normal heart beat, said improvement comprising:
    means, in conjunction with said heart beat detecting means, responsive to an externally applied single energy pulse having a duration which is short compared with the normal demand mode pulse-to-pulse interval to inhibit said pulse generator means from producing a heart-stimulating pulse and to reset said timing means;
    means responsive to a predetermined series of closely spaced energy pulses of similar short duration for inactivating said heart beat detecting means; and
    delay means responsive to cessation of said series of energy pulses for inducing said timing means to operate at said demand mode rate for a predetermined period of time, said inactivating means being operative during said predetermined period of time.

6. The improved pacer recited in claim 5 wherein said energy pulses are selected from the group consisting of magnetic, radio frequency, light and acoustic.

7. The improved pacer recited in claim 5 wherein said energy pulses are magnetic.

8. The improved pacer recited in claim 5 wherein said energy pulses are of radio frequency.

9. The improved pacer recited in claim 5 wherein said energy pulses are acoustic.

10. The improved pacer recited in claim 5 wherein said energy pulses are light.

11. The improved pacer recited in claim 5 wherein said energy pulses are electromagnetic.

12. The improved pacer recited in claim 5 wherein said energy pulses have a duration in the range of 1-5 milliseconds.

13. The improved pacer recited in claim 5 wherein:
    said timing means also has a test mode rate, one of said test mode rate and said demand mode rate being dependent upon remaining useful life of said power source and the other of said test mode rate and said demand mode rate being substantially independent of remaining useful life of said power source, said improvement further comprising:
    means responsive to an externally applied energy source for inducing said timing to operate at said test mode rate, said delay means being responsive to removal of said energy source for inducing said timing means to operate at said demand rate for said predetermined period of time.

* * * * *